US009471870B2

(12) United States Patent
Kao et al.

(10) Patent No.: US 9,471,870 B2
(45) Date of Patent: *Oct. 18, 2016

(54) BRAIN-MACHINE INTERFACE UTILIZING INTERVENTIONS TO EMPHASIZE ASPECTS OF NEURAL VARIANCE AND DECODE SPEED AND ANGLE USING A KINEMATICS FEEDBACK FILTER THAT APPLIES A COVARIANCE MATRIX

(71) Applicant: The Board of Trustees of the Leland Stanford Junior University, Palo Alto, CA (US)

(72) Inventors: Jonathan C. Kao, Stanford, CA (US); Chethan Pandarinath, E Palo Alto, CA (US); Paul Nuyujukian, Stanford, CA (US); Krishna V. Shenoy, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/014,328

(22) Filed: Feb. 3, 2016

(65) Prior Publication Data

US 2016/0224891 A1 Aug. 4, 2016

Related U.S. Application Data

(63) Continuation of application No. 14/309,502, filed on Jun. 19, 2014, now abandoned, which is a continuation-in-part of application No. 12/932,070, filed on Feb. 17, 2011, now Pat. No. 8,792,976.

(60) Provisional application No. 61/338,460, filed on Feb. 18, 2010, provisional application No. 61/837,014, filed on Jun. 19, 2013.

(51) Int. Cl.
G06F 15/18 (2006.01)
G06N 3/08 (2006.01)
A61B 5/04 (2006.01)
A61F 2/72 (2006.01)
G06F 3/01 (2006.01)

(52) U.S. Cl.
CPC ............ *G06N 3/08* (2013.01); *A61B 5/04001* (2013.01); *A61F 2/72* (2013.01); *G06F 3/015* (2013.01); *Y10S 128/905* (2013.01)

(58) Field of Classification Search
CPC .. Y10S 128/905; G06N 3/0445; G06F 3/015
USPC ..................................................... 706/12, 45
See application file for complete search history.

(56) References Cited

U.S. PATENT DOCUMENTS

2003/0093129 A1* 5/2003 Nicolelis et al. ............... 607/45
2013/0018512 A1* 1/2013 Otte ............................ 700/275

(Continued)

OTHER PUBLICATIONS

Wu et al., Modeling and Decoding Motor Cortical Activity Using a Switching Kalman Filter, Jun. 2004 IEEE, pp. 933-942.*

(Continued)

*Primary Examiner* — David Vincent
(74) *Attorney, Agent, or Firm* — Lumen Patent Firm

(57) ABSTRACT

A brain machine interface (BMI) for restoring performance of poorly performing decoders is provided. The BMI has a decoder for decoding neural signals for controlling the brain machine interface. The decoder separates in part neural signals associated with a direction of movement and neural signals associated with a speed of movement of the brain machine interface. The decoder assigns relatively greater weight to the neural signals associated with a direction of movement.

2 Claims, 9 Drawing Sheets

(56) References Cited

U.S. PATENT DOCUMENTS

2014/0058528 A1* 2/2014 Contreras-Vidal et al. .... 623/25
2014/0081423 A1* 3/2014 Palmer et al. .................. 623/39

OTHER PUBLICATIONS

Vallery et al., Reference Trajectory Generation for Rehabilitation Robots: Complementary Limb Motion Estimation, Feb. 2009, IEEE, pp. 23-30.*

Vallery et al., Complementary Limb Motion Estimation based on Interjoint Coordination using Principal Components Analysis, Oct. 2006, IEEE, pp. 933-938.*

Gilja et al., A High Performance neualr prosthesis enabled by control algorithm design, Feb. 2012, Nature Neuroscience, pp. 1752-1758.*

Chestek et al., Neural Prosthetic Systems: Current Problems and Future Directions, Sep. 2009, IEEE, pp. 3369-3375.*

Gilja et al., A brain machine interface control algorithm designed from a feedback control perspective, Sep. 2012, IEEE, pp. 1318-1322.*

* cited by examiner 110     120     130

FIG. 1A     FIG. 1B     FIG. 1C

Offline Perspective

Online Perspective

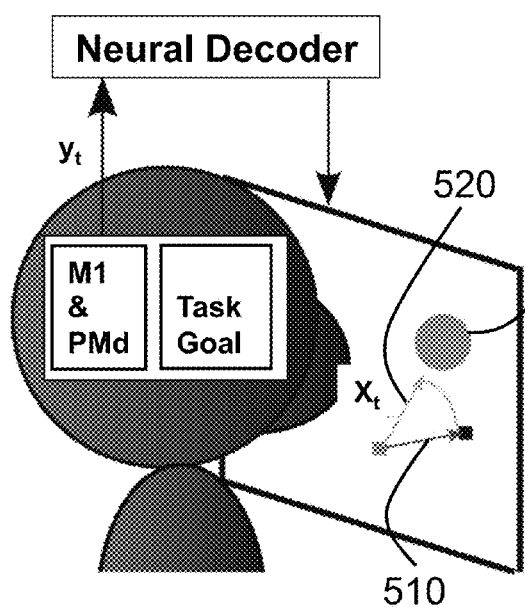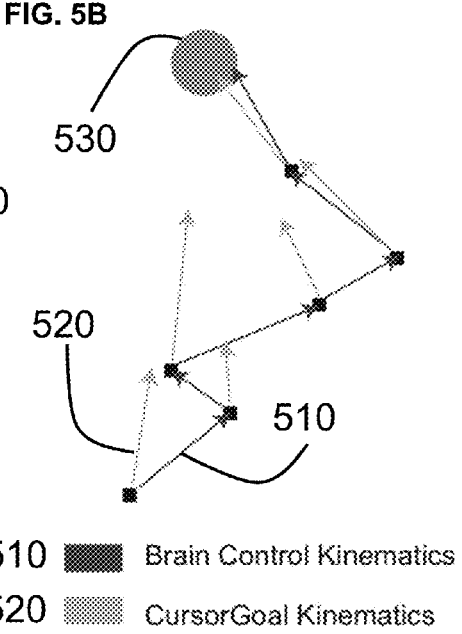
FIG. 5A
FIG. 5B
510 — Brain Control Kinematics
520 — CursorGoal Kinematics

BRAIN-MACHINE INTERFACE UTILIZING INTERVENTIONS TO EMPHASIZE ASPECTS OF NEURAL VARIANCE AND DECODE SPEED AND ANGLE USING A KINEMATICS FEEDBACK FILTER THAT APPLIES A COVARIANCE MATRIX

CROSS-REFERENCE TO RELATED APPLICATIONS

This application is a continuation of U.S. patent application Ser. No. 14/309,502 filed Jun. 19, 2014, which is incorporated herein by reference.

U.S. patent application Ser. No. 14/309,502 filed Jun. 19, 2014 claims priority from US Provisional Patent Application 61/837,014 filed Jun. 19, 2013, which is incorporated herein by reference.

U.S. patent application Ser. No. 14/309,502 filed Jun. 19, 2014 is a Continuation-In-Part of U.S. patent application Ser. No. 12/932,070 filed Feb. 17, 2011, which is incorporated herein by reference.

U.S. patent application Ser. No. 12/932,070 filed Feb. 17, 2011 claims priority from U.S. Provisional Patent Application 61/338,460 filed Feb. 18, 2010, which is incorporated herein by reference.

STATEMENT OF GOVERNMENT SPONSORED SUPPORT

This invention was made with Government support under contract N66001-10-C-2010 awarded by the Defense Advanced Research Projects Agency, and under contracts 8DP1HD075623 and R01NS076460 awarded by the National Institutes of Health. The Government has certain rights in the invention.

FIELD OF THE INVENTION

This invention relates to brain machine interfaces and control of prosthetic devices using neural signals.

BACKGROUND OF THE INVENTION

Brain-machine interfaces (BMIs) translate action potentials from cortical neurons into control signals for guiding prosthetic devices, such as computer cursors and robotic limbs, offering disabled patients greater interaction with the world. BMIs have recently demonstrated considerable promise in proof-of-concept laboratory animal experiments, as well as in human clinical trials. However, two critical barriers to successful translation remain. First, current BMIs move considerably slower and less accurately than the native arm. Second, they do not sustain performance across hours and days, or across behavioral tasks, without human intervention. The present invention addresses this need for increased performance and robustness and advances the art of neural prosthetics.

SUMMARY OF THE INVENTION

In one embodiment of the invention a method is provided for artificial control of a prosthetic device (e.g. a robotic limb, a computer cursor, or the like). A brain machine interface is stored on a computer-readable medium and executable by a computer. The brain machine interface contains a mapping from neural signals to corresponding intention estimating kinematics of a limb trajectory. The intention estimating kinematics includes positions and velocities. The neural signals are signals from cortical neurons related to volitional tasks.

The prosthetic device is controlled by the stored brain machine interface using recorded neural signals as input to the brain machine interface and the stored mapping of the brain machine interface to determine the intention estimating kinematics. The determined intention estimating kinematics then controls the prosthetic device and results in an executed movement of the prosthetic device.

During the control of the prosthetic device, a modified brain machine interface is developed by modifying (and storing by the computer) the vectors of the velocities defined in the brain machine interface. Each of the modifications of the velocity vectors includes changing the direction of the velocity vector towards an end target of the executed movement of the prosthetic device. Once on target, the velocity is set to zero. In one example, the velocity vectors are modified and stored at discrete intervals over the course of the executed movement of the prosthetic device.

The modified brain machine interface includes a new mapping of the neural signals and the intention estimating kinematics that can now be used to control the prosthetic device using recorded neural brain signals from a user of the prosthetic device. In one example, the intention estimating kinematics of the original and modified brain machine interface includes a Kalman filter modeling velocities as intentions and positions as feedback.

In another embodiment of the invention a neural prosthetic is provided having a prosthetic device and a controller. The controller is executable by a computer and interfaced with the prosthetic device. The controller has encoded (and stored on the computer) a mapping of neural signals and kinematics of the prosthetic device. Control kinematics is determined by the controller to control the prosthetic device based on neural signals received from a user of the prosthetic device. In one example of this device, the controller includes a Kalman filter which encodes the velocity kinematics as intentions and position kinematics as feedback.

Another objective of this invention is to significantly increase the performance of poorly performing brain machine interfaces (BMIs) by (i) emphasizing neural variance associated with directional and speed information, (ii) incorporating remembered prior information about the neural data when the BMI did not perform poorly, if available. In one embodiment, this is accomplished by (i) using principal component analysis (PCA) to reduce the dimensionality of the data and downweighting dimensions, which do not have significant directional tuning, and (ii) utilizing previously known information regarding the low-dimensional structure of motor-related cortices. In another embodiment, we also decode speed and angular variables.

A computer-implemented algorithm has two components. First, the algorithm utilizes an intervention on a Kalman filter observation noise process to re-weight certain neural observations. When the neural observations are low-dimensional neural trajectories of the neural data as found via PCA, the intervention can be used to ameliorate directional biases in the decoder by downweighting dimensions that have less information about the directional control of the prosthetic device. Second, the algorithm may utilize prior information regarding the state space that the neural data is projected into. For example, if the space was better sampled when more neurons were previously observed, that space can be remembered; then, in experiments where far fewer neurons are observed, these neurons can be noisily projected into the remembered space. The computer-implemented algorithm may also output, in addition to position and velocity (as in other embodiments described herein) speed and angular variables.

BRIEF DESCRIPTION OF THE DRAWINGS

(FIG. 4B) is a hypothetical plot of parameter setting vs. quality/performance of the resulting system by such a fitting procedure, given the assumptions of the offline perspective, essentially that the maxima for arm reconstructions and BMI control occur with the same parameter settings. In (FIG. 4C) $x_t$ is no longer arm kinematics. Data are collected under closed loop neural control and $x_t$ is the kinematics of the neural cursor. This model fitting procedure assumes that ideal parameter settings for a neural prosthetic and arm reconstructions may vary, as indicated in hypothetical plot (FIG. 4D).

FIGS. 5A-B show according to an exemplary embodiment of the invention methods steps of collecting an "intention-based" kinematic training set: In (FIG. 5A) the user is engaged in online control with a neural cursor. During each moment in the session, the neural decoder drives the cursor with a velocity (vector 510). We assume that the user intended the cursor to generate a velocity towards target 530 in that moment, so we rotate this vector to generate an estimate of intended velocity (vector 520). This new set of kinematics is the modified cursor kinematics training set. (FIG. 5B) is an example of this transformation applied to successive cursor updates.

DETAILED DESCRIPTION

Figure 1:
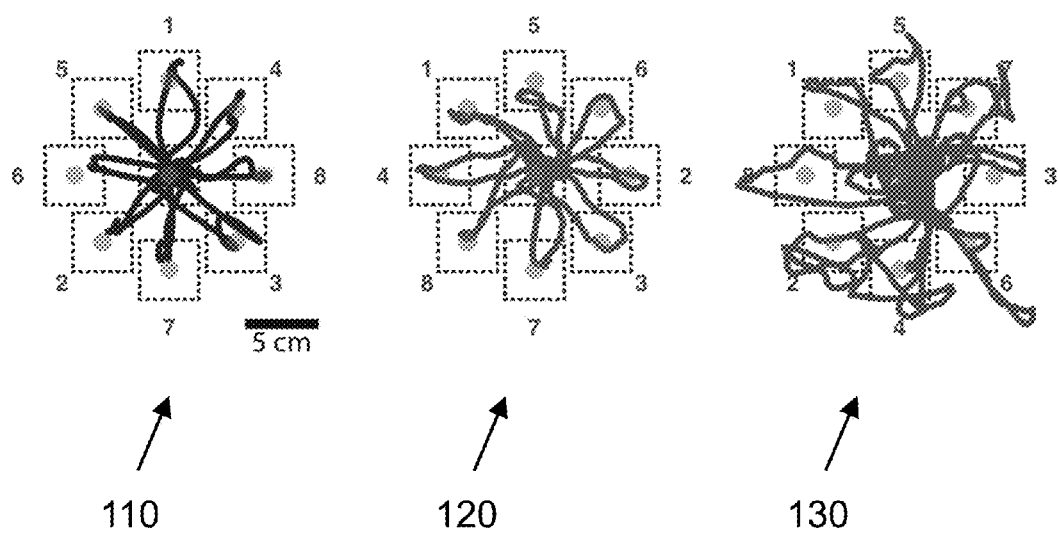
FIGS. 1A-C show [according to an exemplary embodiment of the invention performance comparison between native arm control 110 (FIG. 1A), the control algorithm according to examples of this invention 120 (FIG. 1B), and a current state-of-the-art algorithm 130 (FIG. 1C). Representative traces of cursor path during center-out-and-back reaches. The dashed lines are the target demand boxes for the eight peripheral targets and the central target is within the dashed boxes. Subsequent targets alternated between the center target and the peripheral target in the sequence indicated by the numbers shown. The traces shown are continuous for the duration of all sixteen center-out and return reaches.

In an example of the invention, monkeys were trained to acquire targets with a cursor controlled by either native arm movement or a neural control algorithm. FIGS. 1A-C show representative continuous, uninterrupted cursor movements for three different cursor-control modalities: native arm control 110 (FIG. 1A), the control method according to an embodiment of the invention 120 (FIG. 1B), and an example of a present state-of-the-art velocity Kalman filter (VKF, 130, (FIG. 1C)). Monkeys were required to move the computer cursor to a visual target (inside the dashed boxes) and hold the cursor at the target square for 500 ms to successfully complete a center-out-and-back reaching task and receive a liquid reward. Cursor movements with a controller according to an embodiment of the invention are straighter, faster, and stop better than those generated with the VKF (quantified data not shown). Furthermore, cursor movements produced using the controller according to an embodiment of the invention (120) are qualitatively similar to those produced by the native arm (110).

Figure 2:
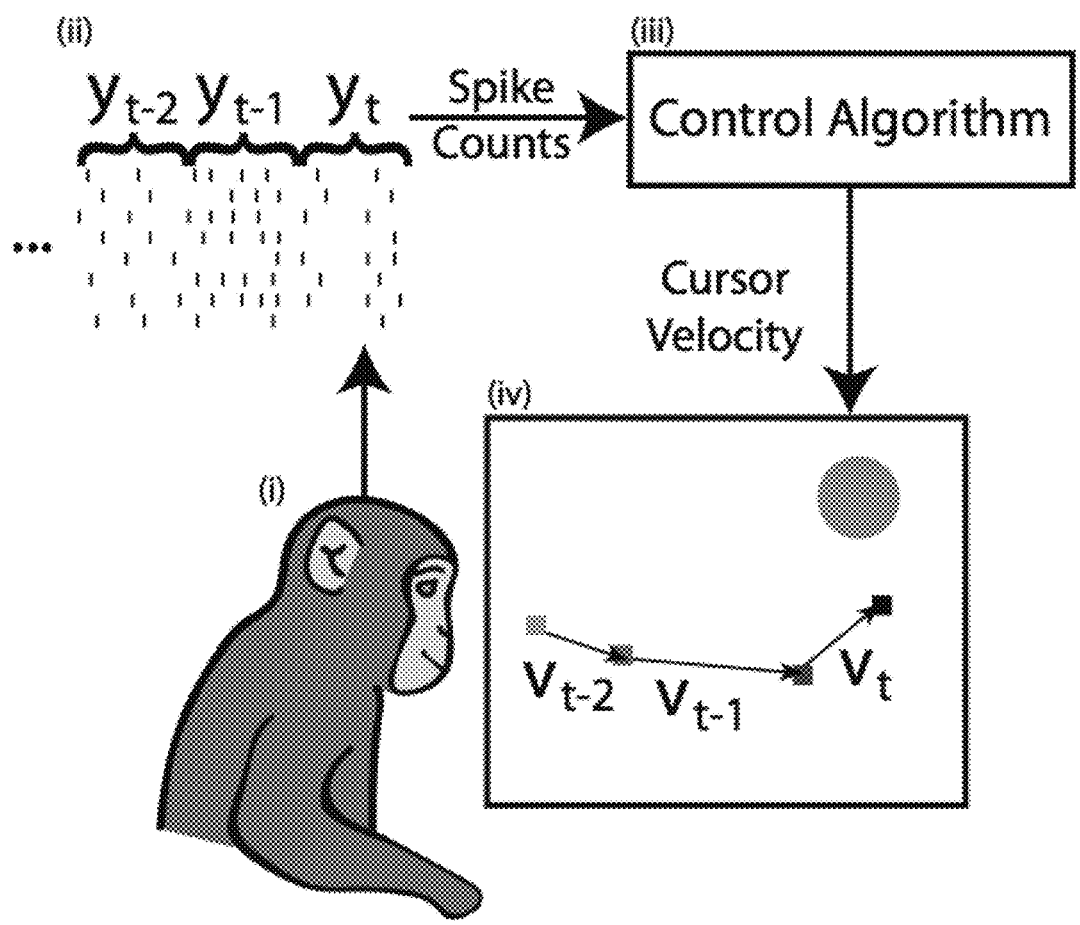
FIG. 2 shows according to an exemplary embodiment of the invention illustrations of an online neural control paradigm and control algorithm training methodology. The input to the neural control algorithm at time t is an array of spike counts, $y_t$, collected from implanted electrodes. The control algorithm translates the incoming neural data into a velocity output $v_t$.

This near native level of performance was achieved by a redefined control algorithm, as well as its training methodology, using a feedback control perspective. As shown in FIG. 2, when an animal is engaged in a brain machine interface (BMI) task the prosthetic device (e.g., computer cursor as shown, or a robotic arm) constitutes a new physical plant with dynamical properties that differ from those of the native arm. The subject controls this new plant by (i) modulating neural signals ($y_t$), which are then (ii) measured and (iii) decoded into a velocity by the control algorithm, which is (iv) used to update the cursor on the screen, affecting neural signals on subsequent time steps. Viewing the BMI from this feedback-control perspective leads to two new methods. The first method is a modification of BMI training method. The second method is an alteration to the design of the control algorithm. These are part of the control algorithm and produce the BMI results 120 in FIG. 1B.

Figure 3:
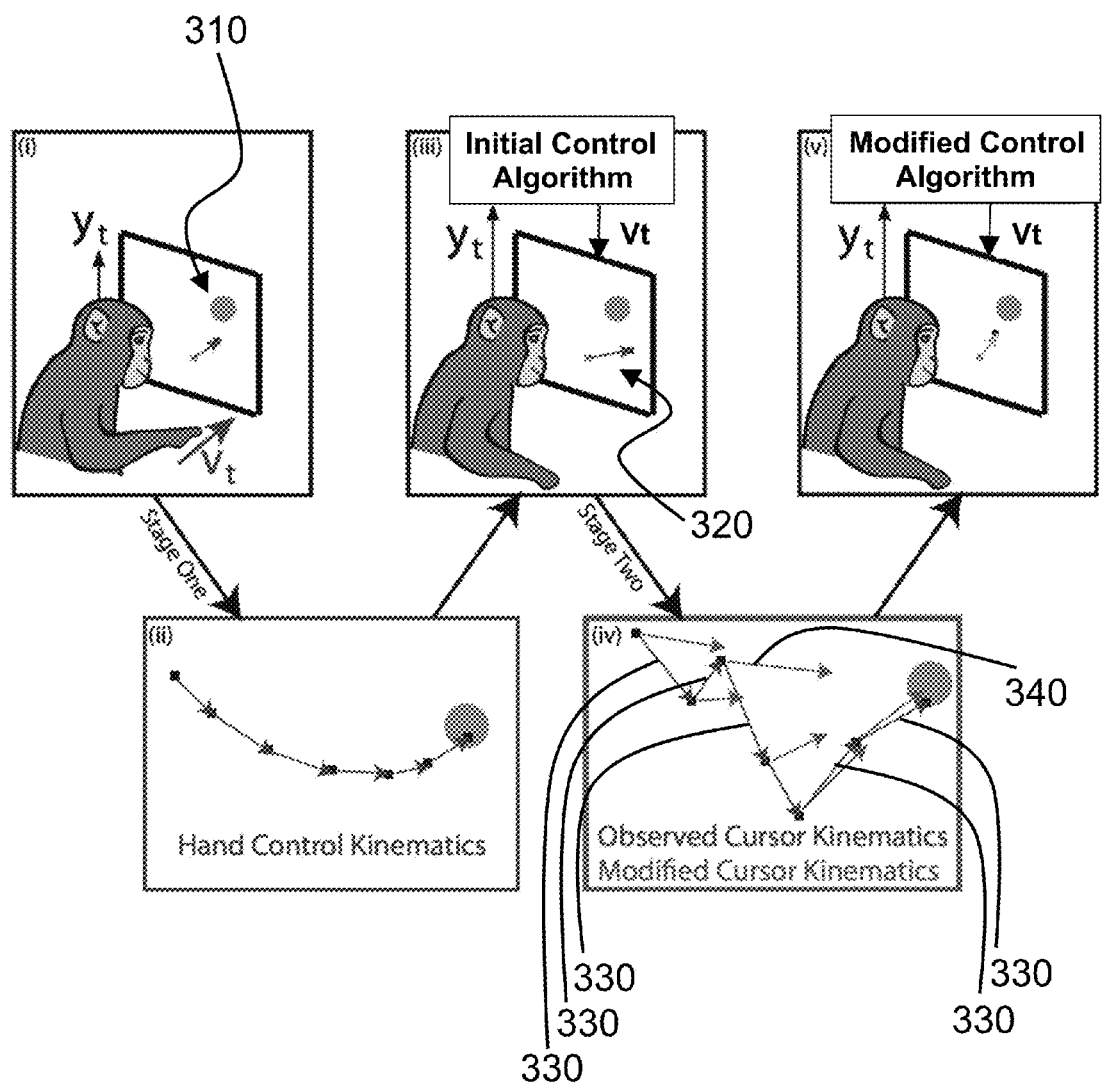
FIG. 3 shows according to an exemplary embodiment of the invention, the neural control algorithm two-stage training method. Initially, cursor kinematics and concurrent neural activity are collected during hand control (i). These kinematics (ii) are regressed against neural activity to generate an initial neural control algorithm. Then, a new set of cursor kinematics and neural activity are collected from closed loop control with the initial algorithm (iii). The cursor kinematics observed with this neural control algorithm (shown by arrows 330 in (iv)) are the BMI algorithm estimates of the monkeys intended cursor velocity. We refine this estimate by rotating the velocities towards the goal (shown in arrows 340 in (iv)—note that only one arrow 340 is indicated for clarity purposes, however any other arrow that is not labeled 330 in iv is considered arrow 340). This set of modified cursor kinematics is regressed against neural activity to generate the modified BMI control algorithm, shown running in closed loop in (v).
Figure 4A:
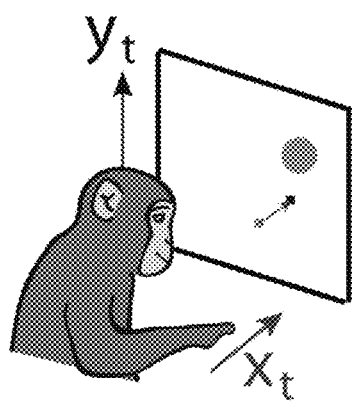
FIGS. 4A-D show according to an exemplary embodiment of the invention a comparison of the offline and online perspectives for neural prosthetic design: In (FIG. 4A) neural data $y_t$ and arm kinematics $x_t$ are collected to fit the parameters of a neural prosthetic.
Figure 4B:
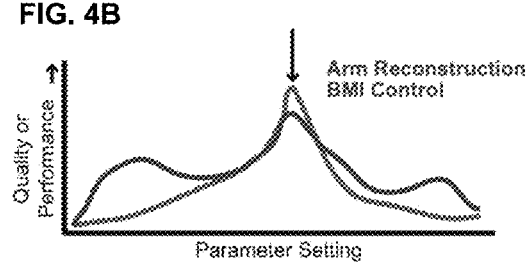
Figure 4C:
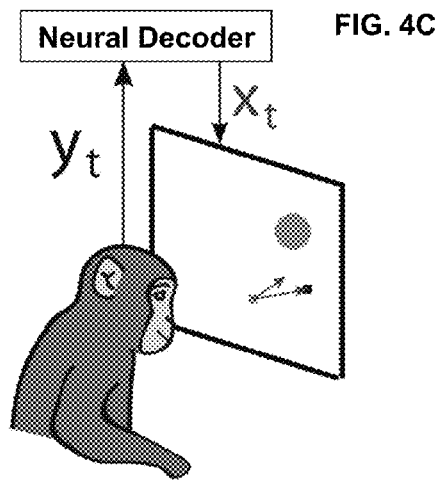
Figure 4D:
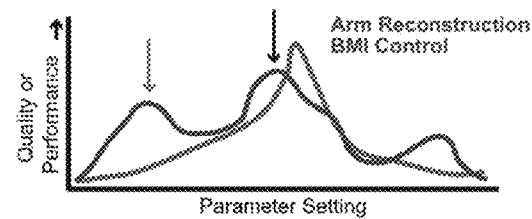

Previously reported control algorithms incorporate a mathematical model built to reconstruct native arm movement kinematics, implicitly assuming that neural control of the arm and prosthetic device are equivalent. However, embodiments of this invention take a different approach and incorporate the fact that the subject's control strategy may actually vary when asked to operate different plants with different dynamics. FIG. 3 outlines the two-stage BMI optimization procedure according to exemplary embodiments of the invention. In the first stage, the monkey controls the cursor using his arm (i in FIG. 3). An initial model is fit using arm trajectories and simultaneously recorded neural signals (ii in FIG. 3). The monkey then controls the cursor using the BMI with this initial model (iii in FIG. 3). This model's cursor trajectories are then refined by incorporating knowledge of the monkey's intention (iv in FIG. 3), leading to a final model (modified BMI) that is used for the remainder of the experiment (v in FIG. 3).

The first method according to an embodiment of the invention is to fit the BMI against a novel set of kinematics. Ideally, instead of fitting neural activity against the kinematics of native arm movements, we fit to the monkey's intended cursor kinematics during closed loop neural control. Since one would lack explicit access to the monkey's intentions, we make the assumption that the monkey always wishes to move towards the target 310, as this is how the native arm moves and is also the best strategy for rapidly acquiring rewards. We employ this assumption to estimate the monkey's intention from cursor movements collected during the initial control session (iii in FIG. 3). Specifically, as shown by iv in FIG. 3, the original BMI cursor movement velocity vectors (320) are rotated towards the target (310). When the cursor is on target, we assume an intention of zero velocity. These modified cursor kinematics and the corresponding neural data are used to fit the modified BMI, thereby arriving at the final control algorithm.

It is important to note that this transformation is applied only to the training data: during online control the BMI has no prior knowledge of the subjects task or goal, or the placement of the targets in the workspace. On subsequent BMI sessions, step-one (arm control) can be skipped (i.e. ii in FIG. 3), and the monkey can begin at step-two (initial BMI control) (iii in FIG. 3) with model parameters from for example a previous day. Although the initial quality of BMI cursor control (arrows 330 in iv in FIG. 3) is often lower on the second day when starting directly with step-two, performance is restored when the model is optimized with the modified cursor kinematics (340, iv in FIG. 3—only one arrow 340 is indicated for clarity purposes, however any other arrow that is not labeled 330 is considered arrow 340). This approach was employed for up to five consecutive days, and performance is on par with that shown in FIGS. 1A-B (110, 120).

The second method attempts to capture the observation that neural activity is correlated with not only the velocity of the cursor but also its position. Most existing BMIs model a relationship between neural firing and either velocity or position. Human clinical trials have shown that BMIs modeling velocity have higher performance. However, if the control algorithm only models the velocity relationship, then a position based increase in firing will result in an increase or decrease in cursor velocity, which is an undesired effect. To mitigate this effect, in one embodiment of this invention, we explicitly model velocity as the users intention, and model position as a signal that is fed back as the user controls the cursor and sees its behavior. This feedback-modified Kalman filter allows the user to control the velocity of the cursor with the measured neural signals while taking into account that this signal is influenced (or corrupted) by the current position of the cursor. Since the BMI knows the position of the cursor it is not estimated from the measured neural signals. Instead, the expected contribution of position to neural activity is removed. This results in a less position-dependent neural data stream, which in turn enables more accurate estimation of the intended cursor velocity as evidenced by higher performance (120 in FIG. 1B).

Long-duration, continuous, high-performance operation is central to the successful translation of BMIs to human patients. To this end, and in further embodiments of this invention, we made three specific design choices for the BMI, in addition to the two methods described supra. First, we did not employ spike sorting, the process of classifying each spike based on the shape of its action potential. The goal of this classification is to separate single channels composed of spikes from many neurons into multiple channels to access the spiking activity of individual neurons. This is a standard practice in neuroscience and also in BMI-design, and can yield the highest information per electrode, but it adds the challenge of tracking each sorted action potential due to changes in amplitude over time. To avoid these signal instabilities, instead of spike sorting, we counted the number of threshold crossings per electrode within a time window. Second, while most BMI designs admit neural data from one or more neural integration time windows (e.g., 100 ms time bin; multiple 50 ms time bins in linear filter with history as far back as 1 sec) we elected to use a single time bin of 50 ms. This was determined through a series of experiments with humans using an online prosthetic simulator (OPS), indicating that shorter time bins are preferable due to their lower latency and therefore reduced closed-loop feedback time. Control experiments with our monkeys performing BMI tasks are consistent with these OPS results. Finally, the number of highly distinguishable single neurons on an electrode array tends to decrease over time, however multiunit activity can often have BMI relevant tuning. The results shown in FIGS. 1A-C were acquired from arrays several months to years post implantation. By employing these somewhat older arrays, which had relatively few clearly distinguishable single units, we were able to confirm that threshold-crossing based multiunit activity together with the control algorithm according to embodiments described herein is able to provide high performance for months and years post array implantation.

These levels of sustained performance and robustness demonstrate the potential to provide functional restoration for patients with a limited ability to move and act upon the world. For patients suffering from neurological injury and disease, although descending pathways are compromised, motor cortex may be intact, permitting the use of this class of technology. In recent years, a number of brain interface technologies using a variety of signal sources, such as the intra-cortical technology described here, electroencephalography (EEG), and electrocorticography (ECoG), have been developed. The BMI community continues to create options for disabled individuals and assess relative risk and benefit. The performance and robustness advances demonstrated herein, as well as the system design methodology, should help increase the clinical viability of intra-cortical based BMIs.

Experimental Methods

In an exemplary embodiment, experiments were conducted with adult male rhesus macaques, implanted with 96 electrode Utah arrays (Blackrock Microsystems Inc., Salt Lake City, Utah) using standard neurosurgical techniques. Monkeys were implanted e.g. 19-27 months or 4-8 months prior to the study. Electrode arrays were implanted in a region spanning the arm representation of the dorsal aspect of premotor cortex (PMd) and primary motor cortex (M1), as estimated visually from local anatomical landmarks.

The macaques were trained to make point-to-point reaches in a 2D plane with a virtual cursor controlled by movements of the contralateral arm or by the output of a neural decoder. The virtual cursor and targets were presented in an immersive 3D environment. Hand position data were measured with an infrared reflective bead tracking system. Spike counts used in all studies were collected by applying a single negative threshold, set to 4.5× root mean square of the spike band of each neural channel—no spike sorting was used. Behavioral control and decoding were run on separate PCs with custom code running on the PC platform, communication latencies between these two systems was 3 ms. This system enabled millisecond timing precision in all computations. Neural data was initially processed by a recording system and was available to the behavioral control system within 5±1 ms. Visual presentation was provided via two LCD monitors with refresh rates at 120 Hz, yielding frame updates within 11±3 ms. The monitors were used to form a Wheatstone stereograph using two mirrors to fuse the two displays into a single stereo percept.

Kalman Filter

Many control algorithms, or continuous decoding methods, have been studied for neural prosthetics applications such as the Kalman filter. The basic intended application of the Kalman filter is to track the state of a dynamical system throughout time using noisy measurements. Although we have a model of how dynamics evolve through time, the underlying system may not be deterministic. If we know the state of the system perfectly at time t, our dynamical model only gives us an estimate of the system state at time t+1. We can use the measurements (or observations) of the system to refine our estimate, and the Kalman filter provides the method by which these sources of information are fused over time. The filter can be presented from a dynamical Bayesian network (DBN) perspective, and is considered to be one of the simplest DBNs.

Figure 6:
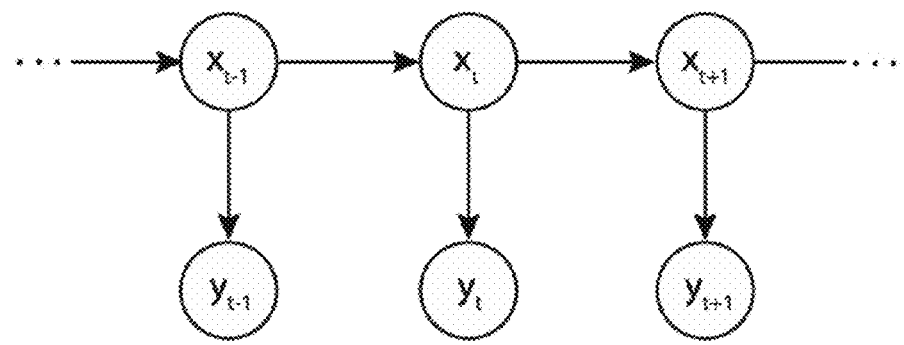
FIG. 6 shows according to an exemplary embodiment of the invention a graphical model representing the assumptions of a Kalman filter. $x_t$ and $y_t$ are the system state and measurement at time t, respectively.
Figure 7:
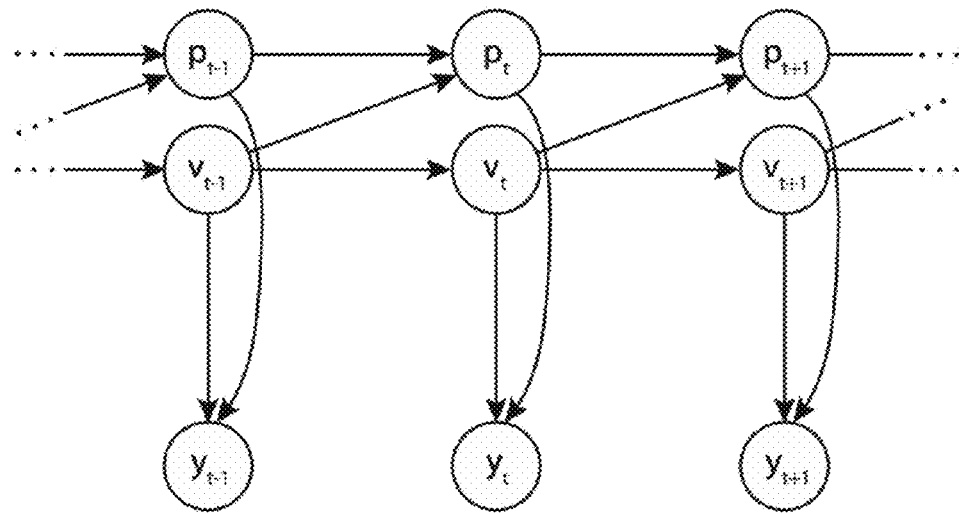
FIG. 7 shows according to an exemplary embodiment of the invention a graphical representation of the position/velocity Kalman filter used for neural control.

A graphical model of the basic DBN representation of the Kalman filter is shown in FIG. 6. For neural prosthetic applications, the system state vector $x_t$ is commonly used to represent the kinematic state. In embodiments of this invention, the state vector represents position and velocity of the cursor:

$$(x_t = [pos_t^{vert}, pos_t^{horiz}, vel_t^{vert}, vel_t^{horiz}, 1]^T)$$

The constant 1 is added to the vector to allow observations to have a fixed offset (i.e., baseline firing rate). $y_t$ is the measured neural signal, which is binned spike counts. The choice of bin width can affect the quality of prosthetic control: assuming local stationarity, long bin widths can provide a more accurate picture of neural state but with poorer time resolution. Thus, there is an implicit tradeoff between how quickly the prosthetic can change state and how accurately those states are estimated. Typical bin widths used in studies range from 10 ms to 300 ms. Through online study, we find that shorter bin widths result in better performance. The results discussed in this study use 25 or 50 ms bin widths.

When applying the standard Kalman filter, the system is modeled with linear dynamics, a linear relationship between kinematic state and neural observations, and Gaussian distributed noise and uncertainty:

$$x_t = A x_{t-1} + w_t \quad (1)$$

$$y_t = C x_t + q_t \quad (2)$$

where $A \in \mathbb{R}^{p \times p}$ and $C \in \mathbb{R}_{q \times n}$ represent the state and observation matrices, and w and q are additive, Gaussian noise sources, defined as $w_t \sim \mathcal{N}(0, W)$ and $q_t \sim \mathcal{N}(0, Q)$. A is the linear transformation from previous kinematic state, or dynamics, and C is mapping from kinematic state to expected observation. This formulation allows for very fast inference (decoding) of kinematics from neural activity and the parameters $\theta = \{A, C, W, Q\}$ can be quickly learned from training data. The observation model of the Kalman filter, C and Q, is fit by regressing neural activity on observed arm kinematics:

$$C = YX^T (XX^T)^{-1} \quad (3)$$

$$Q = \frac{1}{D}(Y - CX)(Y - CX)^T \quad (4)$$

where X and Y are the matrices formed by tiling the D total data points $x_t$ and $y_t$.

For the Kalman filter, we also assume that the dynamics of observed arm kinematics match the desired neural cursor kinematics, and so the parameters of the dynamics or trajectory model, A and W, are fit from observed arm kinematics:

$$A = X_2 X_1^T (X_1 X_1^T)^{-1} \quad (5)$$

$$W = \frac{1}{D-1}(X_2 - AX_1)(X_2 - AX_1)^T \quad (6)$$

$X_1$ is all columns of X except for the last column and $X_2$ is all columns of X except for the first column, introducing a one time-step shift between the two matrices.

In practice we constrain the form of the A and W matrices to obey simple physical kinematics, integrated velocity perfectly explains position:

$$A = \begin{pmatrix} 1 & 0 & dt & 0 & 0 \\ 0 & 1 & 0 & dt & 0 \\ 0 & 0 & a_{vel_{horiz}, vel_{horiz}} & a_{vel_{horiz}, vel_{vert}} & 0 \\ 0 & 0 & a_{vel_{vert}, vel_{horiz}} & a_{vel_{vert}, vel_{vert}} & 0 \\ 0 & 0 & 0 & 0 & 1 \end{pmatrix} \quad (7)$$

After fitting with either set of kinematics, $a_{vel_{vert}, vel_{horiz}}$ and $a_{vel_{horiz}, vel_{vert}}$ are typically close to 0 and $a_{vel_{horiz}, vel_{horiz}}$ and $a_{vel_{vert}, vel_{vert}}$ are less than 1. The resulting model introduces damped velocity dynamics. Therefore, given no neural measurements, we expect a cursor in motion to smoothly slow down. We also constrain the W matrix, so that for the dynamics model, integrated velocity fully explains position:

$$W = \begin{pmatrix} 0 & 0 & 0 & 0 & 0 \\ 0 & 0 & 0 & 0 & 0 \\ 0 & 0 & w_{vel_{horiz}, vel_{horiz}} & w_{vel_{horiz}, vel_{vert}} & 0 \\ 0 & 0 & w_{vel_{vert}, vel_{horiz}} & w_{vel_{vert}, vel_{vert}} & 0 \\ 0 & 0 & 0 & 0 & 0 \end{pmatrix} \quad (8)$$

If we fit the full C matrix, the resulting filter is a position/velocity Kalman filter (neural firing simultaneously describes position and velocity). If we constrain the position terms to be 0, the resulting filter is a velocity only Kalman filter (neural firing describes only velocity).

Kalman Filter Design

Imagine a hypothetical prosthetic that decodes from a single neuron. This neuron fires more vigorously when leftward velocities are instructed and also happens to fire more when the cursor is positioned on the left side of the workspace. If our decoder translates this firing rate into velocities, without any knowledge of positional effects, every time the cursor enters the left side of the screen positive feedback will accelerate the cursor to the left. Positive feedback results because the firing rate increase due to leftward position is mapped to leftward velocity by the decoder, thereby driving the cursor faster to the left than the user intends. By accounting for position, some of the increased firing can be explained by the position of the cursor, and this feedback effect can be mitigated.

However, the way in which the position/velocity Kalman filter models the relationship between position and velocity leads to undesired high frequency jitter in the cursor position. The dynamics model described in the Kalman filter section supra is physically based, acting like an object moving in a gravity free 2-D space with damped velocity, so we may expect cursor position to evolve smoothly. However, the Kalman filter translates velocity uncertainty into position uncertainty at subsequent time-steps. To understand why this occurs, we examine how the filter is run online. At time t we have a previous estimate of the kinematic state, $\hat{x}_{t-1}$ and a new neural observation, $y_t$. The first step in each filter iteration is to apply the dynamics model, estimating $x_t = [p_t, v_t]$ with all neural observations up to time t−1. This is the a priori estimate of $x_t$:

$$\hat{x}_{t|t-1} = A\hat{x}_{t-1} \quad (9)$$

The model also estimates the a priori covariance (or uncertainty) of $\hat{x}_{t|t-1}$:

$$P_{t|t-1} = AP_{t-1}A^T + W \quad (10)$$

We know that the W adds no uncertainty to a priori position, given its structure as defined in Equation 8. However, $AP_{t-1}A^T$ translates previous velocity uncertainty into current position uncertainty. This makes sense: if we do not know the previous velocity with certainty, we do not know the integrated velocity with certainty and so our position estimate may have error. Thus, in practice, there is uncertainty in the a priori estimate of every kinematic variable. To see how this uncertainty in position translates to jitter in the decode, we can continue to step through the algorithm. Once we update the a priori estimate, we must incorporate the information acquired from the neural observation. The model has an expected neural output given $\hat{x}_{t|t-1}$, and this output may not match $y_t$. This error is the measurement residual, $\tilde{y}_t$, and also has a corresponding covariance (or uncertainty) estimate, $S_t$:

$$\tilde{y}_t = y_t - C\hat{x}_{t|t-1} \quad (11)$$

$$S_t = CP_{t|t-1}C^T + Q \quad (12)$$

If this residual is nonzero (which is almost always true in practice), then the measurement and $\hat{x}_{t|t-1}$ do not agree and we must decide how much weight this observation residual has relative to $\hat{x}_{t|t-1}$. This weight is based on how much uncertainty is present in the kinematics suggested by the a priori estimate of $x_t$ versus the kinematics suggested by $\tilde{y}_t$:

$$K_t = P_{t|t-1}C^T S_t^{-1} \quad (13)$$

Finally, we can use $K_t$, called the Kalman gain, to find the estimate of $x_t$ that incorporates all of the neural observations up to time t, this is called the a posteriori estimate. We calculate the a posteriori estimate for $x_t$ and its covariance:

$$\hat{x}_t = \hat{x}_{t|t-1} + K_t \tilde{y}_t \quad (14)$$

$$P_t = (I - K_t C) P_{t|t-1} \quad (15)$$

The Kalman gain transforms the measurement residual into the kinematic space. Since a priori estimates of both position and velocity kinematics have uncertainty and neural measurements have information about position and velocity, the Kalman gain will translate neural measurements into updated a posteriori estimates of both position and velocity. For offline trajectory reconstruction, this makes sense, as this coupled position/velocity uncertainty exists throughout time. However, these assumptions breakdown in the online setting, and substantially limit performance.

We must distinguish online and offline use of the Kalman filter. In the online setting, the user is presented with the a posteriori estimate of cursor kinematics at every time-step. If we believe that the user sees and internalizes the presentation of the cursor on the screen at each time-step, then the way in which we model a posteriori covariance no longer makes sense, as the user accepts the presented position as the current position state. By presenting the decode to the user, we are creating a causal intervention, that explicitly sets the value of the kinematic variable. This operation is defined by probability theory and is well described by the causal calculus.

Figure 8:
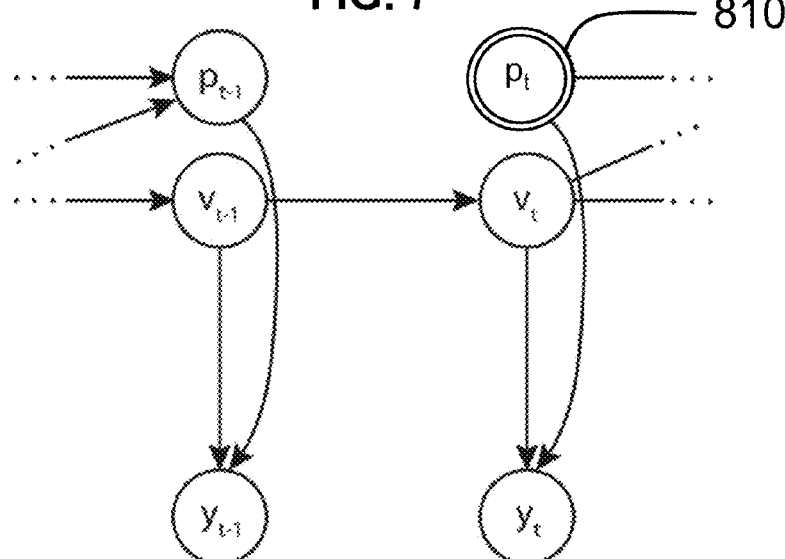
FIG. 8 shows according to an exemplary embodiment of the invention a position/velocity Kalman filter modeling position feedback through causal intervention. In other words, the Kalman filter models velocities as intentions and positions as feedback.

As a first step to modify the filter to incorporate this feedback, we presume that the user internalizes the filter's estimate of cursor position, $\hat{p}_{t-1}$, with complete certainty by time t. Accordingly, $p_t$ is explicitly set to $A_p\hat{p}_{t-1}$, where $A_p$ is the upper-left block of the state matrix A. In other words, since the user knows the previous cursor position $\hat{p}_{t-1}$ via feedback, this forward model is exact at $_{t-1}\hat{x}_t = x_t$. This is shown graphically in FIG. 8, where the intervened variable is shown by 810 (adding another circle is standard notation for causal interventions). Note also that the arrows coming into $p_t$ have been removed, to indicate that $p_t$ has been externally set and uncertainty is not propagated.

The result of this intervention is to remove uncertainty in $p_t$. All parameter fitting methods described in previous sections remain unchanged. To implement this position feedback filter, only a small change in the online operation of the standard filter is necessary. All steps outlined above are the same except for Equation 10. Previously, we had:

$$P_{t|t-1} = AP_t A^T + W \text{ where } P_{t|t-1} = \begin{bmatrix} P_{p,p} & P_{p,v} \\ P_{v,p} & P_{v,v} \end{bmatrix} \quad (16)$$

where each block of the matrix $P_{t|t-1}$ represents the uncertainty propagated from previous kinematic estimates (position to position, position to velocity, and so on). Since we have intervened and set $p_t$ with feedback, this matrix becomes:

$$\bar{P}_{t|t-1} = \begin{bmatrix} 0 & 0 \\ 0 & P_{v,v} \end{bmatrix}. \quad (17)$$

Otherwise, this filter is run in the same manner as the standard Kalman filter.

Figure 9:
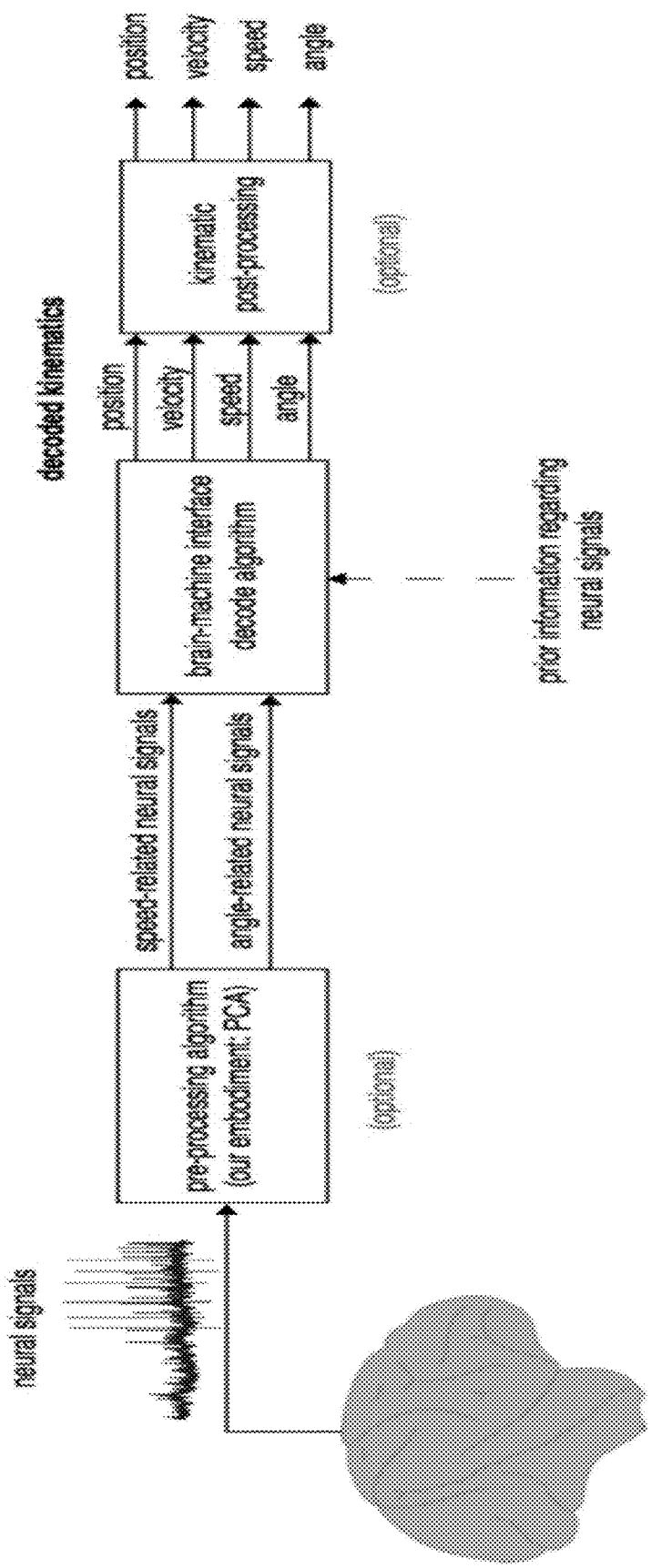
FIG. 9 shows according to an exemplary embodiment of the invention a technique to improve BMI performance after it has degraded significantly due to loss of neural recordings.

Brain-Machine Interface Utilizing Interventions to Emphasize Aspects of Neural Variance and Decode Speed and Angle BMI systems utilize neural recordings to drive prosthetic devices. The performance of BMI systems is important to their clinical viability. Specifically, the highest performing BMIs measure action potentials (spikes) from neurons in motor cortical regions. These systems rely on neural observations from electrode arrays implanted into motor cortical regions. However, the quality of the recordings on the electrodes is known to degrade over time, which in turn degrades the quality of the BMI. In this embodiment of the invention we describe a technique to improve BMI performance after it has degraded significantly due to loss of neural recordings (FIG. 9).

Experimental Approach

In the spirit of addressing the objective of this invention, we modeled (1) a poorly performing decoder, and then subsequently (2) a decoder trained after 25% of available channels (neural recordings) are randomly lost. In one example, we showed that after having lost 25% of channels so that state-of-the-art decoders perform very poorly, the invention (called the intervention PCA algorithm) can recover, and even exceed the performance of state-of-the-art decoders when 100% of the channels were available. Specifically, we compared the intervention PCA algorithm to the highest-reported performing algorithm for 2D cursor control, the ReFIT-KF (Gilj a et al., Nature Neurosci, 2012).

Evaluation Task

Performance was evaluated with the grid task, where the subject can select one of several targets in a grid. This task allows us to quantify performance in terms of the amount of information conveyed in a given time, or the achieved communication rate (in bits per second). Moreover, the task is clinically relevant, since the grid mimics a keyboard. We used the optimal keyboard layout found via optimization, which is a grid of 25 targets with a selection time of 450 ms.

Quality of Observations

To bias ourselves in a regime where decoder performance is poor, we randomly selected N=48 channels from the array as reporting observations of neural spiking. This resulted in a poorly performing decoder. Then, we evaluated the decoder performance after randomly discarding 25% of the previously selected 48 channels, so that there remained N=36 channels. We evaluated the ReFIT-KF (state-of-the-art) when 100% of channels were available and when 75% of channels were available. We evaluated the intervention PCA algorithm (invention) only when 75% of the channels were available.

Choice of Algorithm

The intervention disclosed in this invention can be used with any decoder in which we can easily control the parameters, which map neural observations into prosthetic kinematics. This includes the class of linear BMIs (e.g. simple least-squares regression, Wiener filters, Kalman filters, etc.).

To evaluate what the baseline performance when 100% and 75% of channels were available, we used the ReFIT-KF algorithm (Gilja et al, 2012). The ReFIT-KF algorithm is the highest-performing algorithm for 2D cursor control available in the literature, by almost a factor of 2×. The new algorithm of this invention to recover performance when 75% of the channels are available can be called "intervention PCA-ReFIT KF," or "intervention PCA" for brevity. For the intervention PCA decoder, we used as observations the low-dimensional projections (found via PCA) of the neural data. This means that the activity of N channels is projected into a D dimensional space, where D<N, and treated as the neural observations of the BMI. The details of the intervention PCA algorithm are discussed in section 2. Inspired from the intervention PCA approach, we also discuss how a decoder can be modified to output, in addition to the position and velocity of the prosthesis, the speed and direction of the prosthesis.

Intervention PCA

The intervention PCA algorithm leverages scientific knowledge of the low-dimensional nature of neural data. For the intervention PCA algorithm, we modified the ReFIT-KF algorithm by making the observations of the Kalman filter the principal components of the data (as opposed to binned spike counts) and performing an intervention on the noise models, which is discussed in more detail below.

Projection to Reproduce Original Trajectories

When 100% of the channels were available, we used dimensionality reduction (via PCA) to compute the low-dimensional "canonical" neural trajectories. These trajectories represent the projection of all the neural activity into a lower-dimensional space. When only 75% of the available channels remained, we performed a regression so that the remaining 75% of neural data attempted to reproduce the canonical trajectories (remembered from when 100% of the neural data was available). Therefore, we learned a matrix which mapped the neural data into a low-dimensional space (albeit noisily) so that the neural trajectories (which are the observations of the BMI) approximate the neural trajectories when 100% of the channels were available. This was performed by least-squares regression.

Move-Stop Variance is Largely Contained in the Top Principal Components of the Data Whether the subject is moving or stopping the prosthetic device is a large variance event, evidenced by a general rise in firing rates across many channels. Because this event (capturing the speed of the prosthesis) is of large variance, and present in a significant proportion of channels, much of this variance is present in the top principal components (PCs) of the neural data since they reflect dimensions capturing the greatest amount of neural variance.

In linear BMI systems, this means that $PC_1$ typically contributes a large velocity to the decoder. However, due to the limitations of linear techniques used for BMIs, if one is decoding velocity, then $PC_1$ contributes a large magnitude speed in only one direction. In the case of decoders with lower performance, this can severely bias the decoder, if there is not much directional tuning in $PC_1$. This is because a large projection of the data in $PC_1$ will drive the decoder in a certain direction with significant magnitude, even though it has little directional tuning.

The Kalman Filter Weighs Observations in Accordance to the Observation Process Noise Although this technique could be applied to other types of linear filters, we will discuss its particular application to Kalman filters (and will briefly mention an example of how to achieve a similar effect in other linear techniques). We specifically address Kalman filters because they are the highest-performance algorithms reported in literature for 2D cursor control.

State-of-the-art BMIs are based on velocity Kalman filters (VKFs), which decode an underlying state $x_k$ (a vector denoting the velocity of the cursor), and the observations $y_k$ (a vector denoting the neural observations). These Kalman filters operate on a linear dynamical system (LDS) of the form:

$$x_{k+1} = Ax_k + w_k$$

$$y_k = Cx_k + q_k$$

where $w_k \sim N(0,W)$ and $q_k \sim N(0,Q)$. For intervention PCA, where the $(y_k)$ are the principal components of the neural data, $(y_k)_i$ refers to $PC_i$.

The observation noise covariance, Q, models the covariance in the observation process, $y_k = Cx_k$. Hence, if $Q_{11}$ is relatively large, it heuristically indicates that estimating the first dimension of the observation, $(y_k)_1$ with the underlying state, $(C_{1,:})x_k$, is noisy (where $C_{1,:}$ is the first row of C). Therefore, the first dimension of the observation is relatively unreliable. The intervention will decrease the reliability of the observation of $PC_1$ which decreases its contribution to the decoder. With the VKF, this is possible by increasing $Q_{11}$. In other linear techniques, e.g. if there is a single matrix mapping L which calculates $x_k = Ly_k$, it is possible to down-weight the observation $(y_k)_1$, by scaling the coefficients in the first column of L by a constant between 0 and 1.

The Intervention PCA Decoder can Increase the Performance of Poorly Performing Decoders The goal of the intervention PCA decoder is to mitigate degrading decoder performance, specifically by ameliorating biases that typically cripple decoders. In our particular experiments, intervention PCA addresses this by increasing the observation noise of $PC_1$ in a Kalman filter (although we allow the possibility of doing this for other principal components, e.g. $PC_2$). This effectively downweights the contribution of $PC_1$ to the decoder. As previously mentioned, the main motivation for downweighting $PC_1$ is because $PC_1$, through the KF, contributes a large speed in a certain direction by virtue of being a large variance event associated with moving and stopping of the cursor. Hence, even if $PC_1$ has little directional tuning, due to the Kalman filter modeling, it contributes a massive speed in a single direction by the modeling of the Kalman filter. Thus, by downweighting the contribution of $PC_1$, we ameliorate any major bias that may arise from such modeling assumptions. We reiterate that this technique is not limited to Kalman filters.

It should be noted that the intervention PCA decoder is not merely downweighting the observations relative to the kinematics model of a VKF, $x_{k+1} = Ax_k + W_k$. That is, it is not merely increasing the momentum of the cursor. In fact, the amount of weight given to observations relative to the kinematic model is approximately equal between intervention PCA and ReFIT-KF. Instead, what the intervention PCA decoder is doing is differentially weighing aspects of neural variance. If $PC_1$ does not have large directional variance, but large speed (move/stop) variance, then downweighting $PC_1$ would allow other dimensions, which may have more directional tuning, to be more prominent in the decoder. Hence, by using PCA, we are able to do a global downweighting (affecting all channels), varying for each channel, as they contribute to the dimension of interest. In this sense, the low-dimensional projection can be viewed as approximately partitioning aspects of neural variance into different dimensions; we then perform an intervention to downweight certain dimensions. It should be noted that other dimensionality reduction techniques which separate aspects of neural variance could be used, so that the technique is not limited to PCA. Although PCA is not guaranteed to partition the speed (move-stop) vs directional variance amongst different dimensions, we have causally shown that $PC_1$ contains a sufficient amount of information to determine whether the subject is moving or stopping, and is the largest contributor to velocity. Hence, there is approximate variance organization resulting through PCA, which allows us to differentially attenuate a dimension with less directional tuning (and more to do with speed variance) relative to other dimensions. This increases the performance of poor decoders.

Intervention PCA Results

Figure 10:
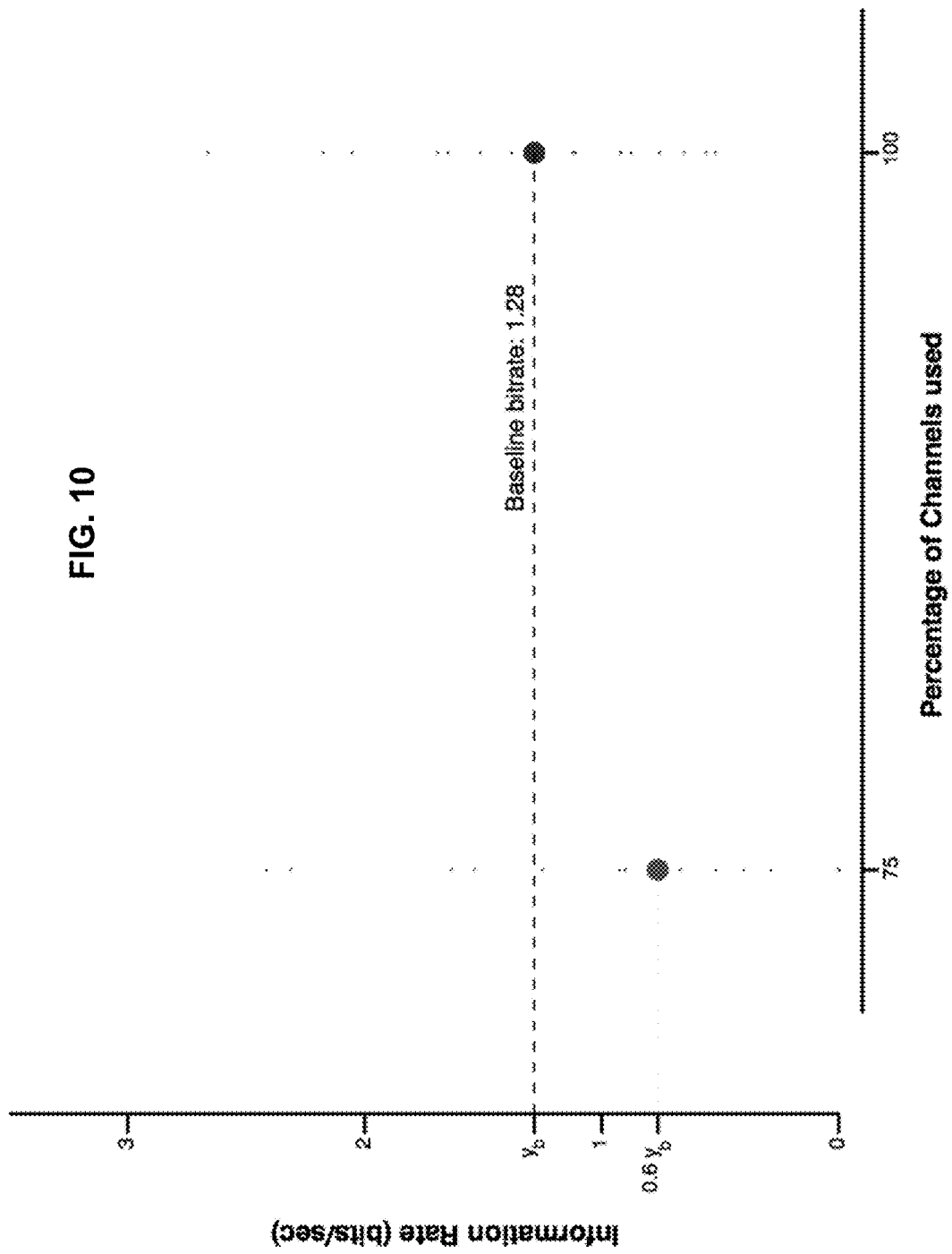
FIGS. 10-11 show according to an exemplary embodiment of the invention intervention PCA results. The performance of the intervention PCA algorithm 1110 is superior to the state of the art decoder.

First, we showed (FIG. 10) that the performance of ReFIT-KF degrades after dropping 25% of the channels randomly. We evaluated the performance of ReFIT-KF when 100% of channels were available. Where red denotes the performance of the state-of-the-art ReFIT-KF, each small dot denotes the bitrate of an experimental block where the subject used a decoder to select targets on a grid, while the large dot denotes the mean bitrate across all experimental blocks. When 100% of the channels were available, the variance in performance was due to variance in subject performance within a day, and then across days. Then, we evaluated the performance of ReFIT-KF when x=75% of channels were available, to show that the performance degrades with more channel loss. For each experimental block (small dot), we randomly selected 25% of the channels and subsequently dropped them, so that each block has a different set of channels dropped. We note that dropping 25% of the channels leads to approximately 60% of the performance on the grid task (compared to when 100% of the channels were available).

Figure 11:
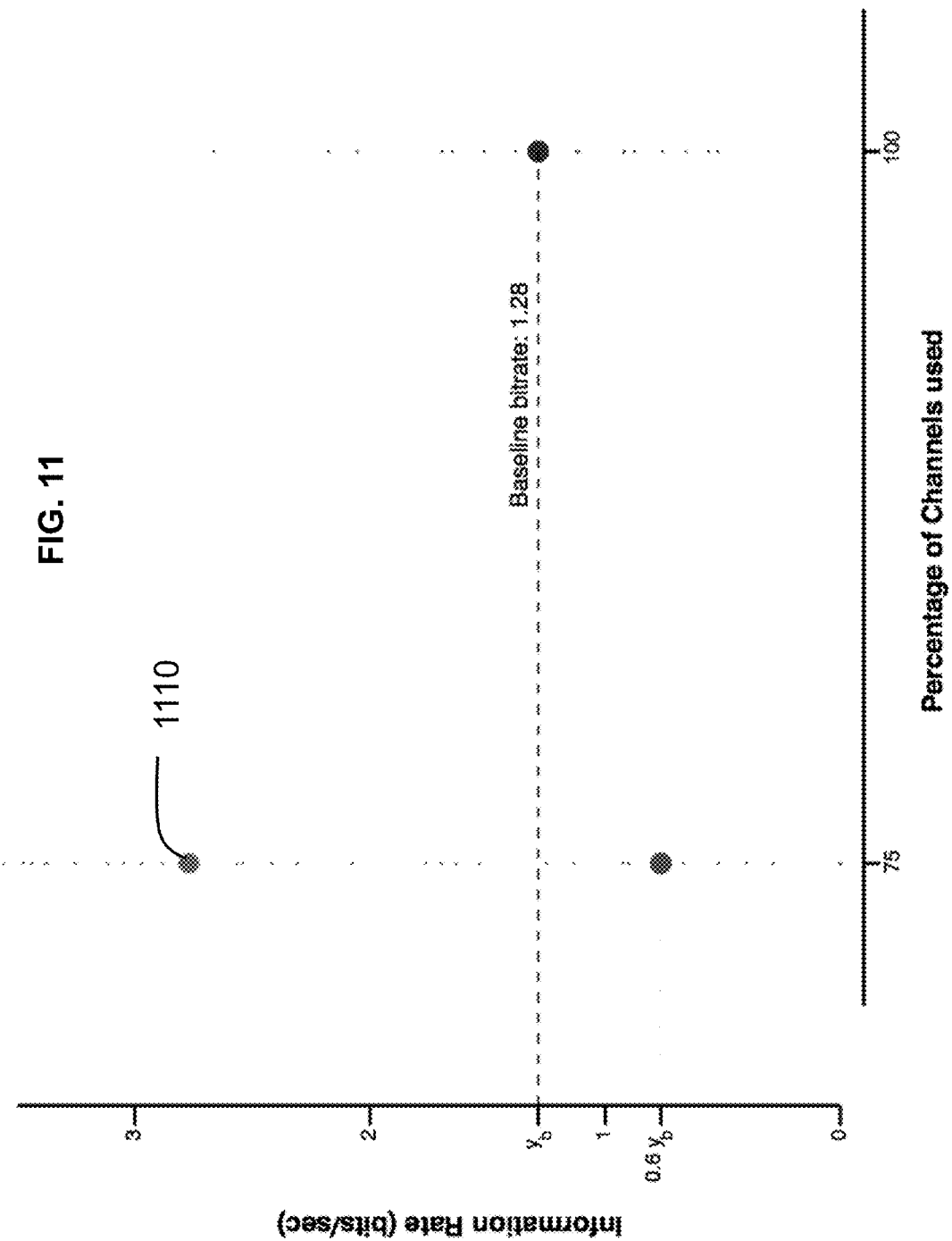

Next we show (FIG. 11) the performance of intervention PCA (1110) for the same experimental blocks where 25% of the channels were randomly lost. We note that intervention PCA recovers performance, and indeed surpasses the performance of ReFIT-KF at 100% of the channels.

Decoding Speed and Angle

Inspired by the intervention PCA results, we also evaluated the feasibility of building a decoder that regresses the neural data against the desired speed and angle of the prosthesis (as opposed to the Cartesian velocity and position) and outputs these variables to a kinematic space. Thus, the dimensions of the output kinematic space (i.e., speed and angle) are independently and separately estimated such that they are not derived from Cartesian velocities. Note that prior algorithms would necessarily have to combine the independent dimensions estimated by the decoder to arrive at speed and angle, since they do not estimate these variables separately and independently.

Thus, we separately and independently decoded the speed and angle of the prosthesis rather than the Cartesian velocity of the prosthesis. In one embodiment, we separately and independently decoded the speed by making it the state of the Kalman filter (rather than the Cartesian velocity). After decoding a speed variable, s, we allowed the speed to be transformed according to a non-linear function, $s''=f(s)$. In one embodiment, this non-linear function was a piece-wise linear function that amplified higher speeds. To decode the angle, $\theta$, of the prosthesis, in two embodiments, we decoded both the $\sin(\theta)$ and $\cos(\theta)$ of the prosthetic device using either a Wiener filter or a Kalman filter. Then the direction of movement could be calculated as $\theta = \arctan(\sin(\theta)/\cos(\theta))$ or the x- and y-velocities could be calculated as $s'' \cos(\theta)$ and $s'' \sin(\theta)$ respectively.

REFERENCE (1) V. Gilja, P. Nuyujukian, C. A. Chestek, J. P. Cunningham, B. M. Yu, J. M. Fan, M. M. Churchland, M. T. Kaufman, J. C. Kao, S. I. Ryu, and K. V. Shenoy, "A high-performance neural prosthesis enabled by control algorithm design," Nature Neuroscience, vol. 15, pp. 7-10, November 2012.

What is claimed is:

1. An artificial controller of a prosthetic device, comprising:
    (a) a brain machine interface having an algorithm executable by a computer, wherein the brain machine interface comprises a mapping from neural signals to corresponding intention estimating kinematics of a limb trajectory, wherein the intention estimating kinematics comprises speeds and angles;
    b) the brain machine interface controlling the prosthetic device using recorded neural signals as input to the brain machine interface and the mapping of the brain machine interface determining the intention estimating kinematics to control the prosthetic device, wherein the controller results in an executed movement of the prosthetic device;
    (c) a modified brain machine interface having an algorithm executable by the computer for modifying during the control of the prosthetic device, at discrete time intervals over the course of the executed movement of the prosthetic device, the angles in the brain machine interface, wherein each of the modifications of the angles comprises changes in the direction of the angles towards an end target of the executed movement of the prosthetic device;
    (d) the modified brain machine interface controlling the prosthetic device; and
    (e) a kinematics feedback filter executable by the computer in both the brain machine interface and the modified brain machine interface, wherein the kinematics feedback filter applies a covariance matrix of an a posteriori estimate of the intention estimating kinematics at each time step of the discrete time intervals, whereby the kinematics are modeled as feedback from the interfaces to a user of the prosthetic device.

2. The artificial controller as set forth in claim 1, further comprising an algorithm for projecting the neural signals into a space of lower dimensionality compared to the dimensionality of the neural signals, and re-weighting the contribution of the dimensions of the lower dimensional space to the estimated kinematics.

* * * * *